United States Patent [19]

Petit et al.

[11] Patent Number: 5,688,929
[45] Date of Patent: Nov. 18, 1997

[54] SURFACE ACTIVE GALACTURONIC ACID DERIVATIVES

[75] Inventors: Serge Petit, Montmaco; Robert Ralainirina, Amiens; Serge Favre, Compiegne; Régis De Baynast, Versailles, all of France

[73] Assignees: Agro Industrie Recherches et Developpements (A.R.D.), Paris, France; Zschimmer & Schwarz GmbH & Co. Chemische Fabriken, Lahnstein, Germany

[21] Appl. No.: 975,546

[22] PCT Filed: Jul. 17, 1992

[86] PCT No.: PCT/FR92/00701

§ 371 Date: Feb. 18, 1993

§ 102(e) Date: Feb. 18, 1993

[87] PCT Pub. No.: WO93/02092

PCT Pub. Date: Feb. 4, 1993

[30] Foreign Application Priority Data

Jul. 22, 1991 [FR] France .................. 91 09226

[51] Int. Cl.$^6$ .................. C07G 3/00; C07G 11/00
[52] U.S. Cl. .................. 536/4.1; 536/18.5
[58] Field of Search .................. 536/4.1, 18.5

[56] References Cited

U.S. PATENT DOCUMENTS

| | | | |
|---|---|---|---|
| 3,873,614 | 3/1975 | Lamberti | 562/537 |
| 4,335,236 | 6/1982 | Tsuyumu et al. | 536/18.2 |
| 4,713,447 | 12/1987 | Cotton | 536/4.1 |
| 4,950,743 | 8/1990 | McCurry Jr. et al. | 536/18.5 |
| 5,079,350 | 1/1992 | Fujita et al. | 536/18.5 |
| 5,166,337 | 11/1992 | Ripke | 536/4.1 |
| 5,223,411 | 6/1993 | Plusquolke et al. | 536/4.1 |

FOREIGN PATENT DOCUMENTS

| | | |
|---|---|---|
| 334498 | 3/1988 | European Pat. Off. |
| 326673 | 8/1989 | European Pat. Off. |
| 427210 | 5/1991 | European Pat. Off. |

OTHER PUBLICATIONS

Bocker et al, "Synthese und Eigenschaften von Kohlenhydratensiden", Tenside Surf. Det. 26 (1989) 5, pp. 318–324.
Hui et al, "Synthesis of glucoside surfactants and asymmetric reduction of phenyl alkyl ketones in chiral micelles", Chemical Abstracts, vol. 109, 1988, Abstract No. 190679t.

Namba et al, "Liposomal modification with uronate, which endows liposomes with long circulation in vivo, reduces the uptake of liposomes by J744 cells in vitro", Life Sciences, vol. 50, 1992, pp. 1773–1779.

*Primary Examiner*—David M. Naff
*Assistant Examiner*—L. Blaine Lankford
*Attorney, Agent, or Firm*—Cushman Darby & Cushman Intellectual Property Group of Pillsbury Madison & Sutro LLP

[57] ABSTRACT

The galacturonic acid derivatives of formula:

$$R-\underset{\underset{H}{\overset{|}{C}}-\underset{OH}{\overset{|}{C}}}{\overset{\overset{O}{\diagdown}}{\overset{|}{\underset{|}{C}}}\underset{OH}{\overset{H}{\diagup}}}\overset{OR_1}{\underset{H}{\diagdown}}C$$ (I)

R1 being a linear or branched alkyl having 2 to 22 carbon atoms,

R being:

$$\diagup CH-CH(OH)-CO_2R_2$$

or $$-CH(OH)-CH-CO_2R_2$$

for which the carbon carrying the hydroxyl group is attached to the endocyclic oxygen atom.

R2 being hydrogen, R1, an alkali metal atom, an alkaline-earth metal atom or a quaternary ammonium group of formula:

$$-N{\diagup}{\overset{R_3}{\underset{\underset{R_6}{R_5}}{R_4}}}$$

in which R3 to R6 is each independently of the other hydrogen, an alkyl having 1 to 6 carbon atoms or a hydroxyalkyl having 1 to 6 carbon atoms, are surface-active agents.

8 Claims, No Drawings

SURFACE ACTIVE GALACTURONIC ACID DERIVATIVES

The present invention relates to galacturonic acid-derivatives, methods for preparing them and their various applications, especially as nonionic or anionic surface-active agents.

The grafting of alkyl groups on carbohydrates leads to surface-active agents whose surface-active properties are very valuable and whose biodegradability is generally good (R. D. SWISHER, "Surfactant biodegradation", Marcel Dekker, Inc. New York, 1987).

The most widely used raw materials are sucrose and glucose and the reactions performed on these unprotected substrates lead to complex mixtures of nonionic surfactants, this being due to random grafting (mono-,di- and triaddition) and to inter- and/or intramolecular oligomerization phenomena (see EP 0249013, DE 3842541, DE 3723826, H. LUDERS and P. HOFFMANN "Synthesis, Chemical Structure and Properties of Alkylpolyglucosides", Césio, 2nd International Congress on Surfactants, 24–27 May 1988, PARIS, and D. BALZET "Alkylpolyglucosides, their physicochemical properties and their uses", Tenside Surf. Det. 28, 1991, 6). The reaction temperatures used in these preparations are generally high (above 100° C.), which leads to partial degradation of the substrates and causes coloration of the products.

In the case of carbohydrate-based anionic surfactants, the rare compounds described in the literature are obtained by bioconversion (lipid-containing sophoroses, rhamnolipids and the like: see DE 3526417; G. Georgiu, S. C. Lin and M. M. Sharma, "Surface active compounds from microorganisms", Bio./Biotechnology, Vol. 10, January 1992, 60–65; D. F. Gerson and J. E. Zajic "microbial biosurfactants", Process Biochemistry, July 1979, 20–29; D. G. Cooper "Biosurfactants", Microbiological Sciences, Vol. 3, No. 5, 1986, 145–149) or by oxidation of the primary hydroxyl of D-octylglucopyranoside, α-D-dodecylglucopyranoside, α-D-tetradecylglucopyranoside, β-D-decyimaltoside and α-D-tetradecylmaltoside (see EP 0326673; Bocker J. Thiem J., Tenside, Surf, Det., 26, 318, (1989); Van Bekkum H. in "Carbohydrates as organic raw materials" Lichtenthaler F. W. (Ed), V. C. H. Weinheim 289 (1991) and references cited; GOEDE A. T. J. W., de Wit P., Vinki P., Van Rantwijk F. and Van Bekkum H., presentation at the 6th European Congress on the chemistry of carbohydrates, Edinburgh, 1991), either catalytically, or chemically with sulphur/pyridine trioxide complex [see Miam H., Anderson C. E. and Kent P. W., Biochem. J., 181, 387, (1979)] to give the corresponding carboxylated or sulphated compounds respectively. These documents do not describe galactose derivatives nor their properties, of course, in spite of dangerous generalizations. Furthermore, the substrates required for these syntheses are difficult to obtain and the only procedures leading to compounds with well-defined structures always require prior protection, use organic solvents and expensive reagents (silver carbonate); such is the case in particular for octyl glucoside and its homologues (see Rosayear P., van Aken T., Baxter J., Fergusson-Miller S., Biochemistry 19, 4108, 1980; Shimamoto T., Saito S., Tsuchiya T., J. Biochem., 97, 1807, 1985; Schmidt R. R., Angews Chem. Intern. Ed. Engl., 25, 212, 1986; Straathof A. J. T., Romein F., van Rantwijk F., Kieboom A. P. G. and van Bekkum H., Starch, 39 (10), 362, 1987).

These techniques do not meet the current demand for nonionic surfactants (especially forming a two-phase system), or anionic surfactants, which can be prepared at low cost and with greater efficacy than those used up until now.

Recent attempts (D. Plusquellec and colleagues, Anal. Bioch. 179, 145 (1989); EP 334498; EP 427210, F. Bjorkling and colleagues, J. Chem. Soc., Chem. Commun. 934 (1989); K. Adelhorst and colleagues, Synthesis, 112–115 (1989); M. P. de NiJs and colleagues, Recl. Tray. Chim., The Netherlands, 109, 429–433 (1990), enable nonionic surface-active agents of well-defined structure to be obtained, and without protection of the hydrophilic substrate. However, they require a chemical glycosilation step and an enzymatic step which enables the grafting of a second alkyl group at the primary alcohol position of glucose. The main disadvantages of such a technique lie in the limitations presented by lipases which accept well only certain glucoside substrates and whose grafting yields vary widely depending on the length of the fatty acid or ester involved in the reaction. While in a few very favorable cases the yields may be as high as 60%, they are more generally less than 20%. Furthermore, the cost of the enzymatic treatment is far from being negligible and the preparation of an alkyl glycoside substrate of high purity is not an easy operation.

Moreover, the compounds described, especially in EP 427210 (Lion Corporation) and EP 334498 (Cerestar Holding), are different from those of the present invention since they are obtained by (enzymatic) esterification, by a fatty acid, of the primary hydroxyl position of alkyl glucosides. The generalization, which is in fact dangerous (given the specificity of the enzymatic catalysis), of this technique to hexoses as a whole would not lead, even for the "galactose" series, to the compounds which are the subject of the invention.

Indeed, the two-component compounds which these authors would have obtained for the "galactose" series would be of the following general structure:

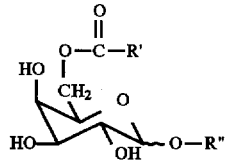

whereas the "pyranose" isomers of the present invention are of the general structure:

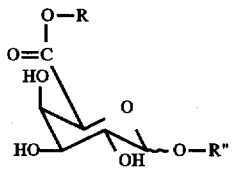

The invention relates to galacturonic acid derivatives which may be prepared purely by chemical means, without the phenomenon of oligomerization and without prior protection but with perfect regio-selectivity and high yields, and which are endowed with properties, especially surfactant properties, superior to those of the best surfactants used up until now.

The subject of the invention is galacturonic acid derivatives of formula:

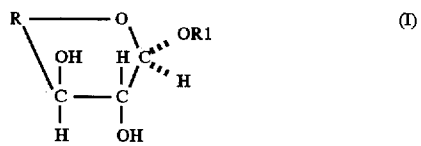

R1 being a linear or branched alkyl having 2 to 22 carbon atoms,

R being:

or

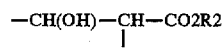

for which the carbon carrying the hydroxyl group is not attached to the endocyclic oxygen atom.

R2 being hydrogen, R1, an alkali metal atom, an alkaline-earth metal atom or a quaternary ammonium group of formula:

in which R3 to R6 is each independently of the other hydrogen, an alkyl having 1 to 6 carbon atoms or a hydroxyalkyl having 1 to 6 carbon atoms.

The alkali metal is in particular sodium and potassium, and the alkaline-earth metal is magnesium. 2-Methyl-2-hydroxymethylethylammonium, tri(hydroxymethyl) methylammonium and 2,2-(dihydroxymethyl) ethylammonium may be mentioned as quaternary ammonium salts.

Of these derivatives, those in which R1 is an alkyl having 8 to 14 carbon atoms, in particular dodecyl galactoside uronic acid salts whose foaming power is greater than the conventional reference products, are preferred because of their good foaming power. The evaluation is performed according to the NFT 73404 standard which consists in allowing 500 ml of a solution of surfactant to flow, at a steady rate, into a thermostatted 1000 ml graduated cylinder containing 50 ml of the same solution. The amount of foam generated by the flow is volumetrically estimated immediately after the flow has stopped (the parameter measured is the initial foam volume).

The stability of the foam is also taken into account by measuring the volume over 20 minutes.

Sodium dodecyl D-galactoside uronate is more effective than sodium dodecylbenzenesulphonate (SDBS), sodium dodecyl sulphate (SDS) or sodium lauryl ether sulphate containing 2 moles of ethylene oxide (LES), its initial foam volume is 520 ml whereas it is not more than 450 ml for the others.

Their foaming power is substantially equal to that of alkyl polyglucosides (APG) whose costs, because of their production and purification process (linked in particular to problems of coloration and stability of the product in a basic medium), are more than twice those for the derivatives of the invention.

Moreover, these compounds exhibit a very good foam stability over time since the percentage loss is less than 5% after 20 minutes.

Octyl galactoside uronic and decyl galactoside uronic acid salts also have good wetting power which is greater than that of sodium lauryl ether sulphate containing 2 moles of ethylene oxide (LES), sodium dodecyl sulphonate (SDS) and alkyl polyglucosides (APG) after 400 seconds. The test performed consists in monitoring, for 600 seconds, the amount of surfactant solution absorbed by a cotton fabric. The piece of fabric comes slightly into contact with the surface of the surfactant solution and the traction generated by the capillary rise of the solution is recorded continuously for 600 seconds.

The fabric used is a grey cotton cloth cut into pieces of (2 cm by 2 cm, equivalent to about 0.12 g), and meeting the requirements of the NFT 73406 standard. The apparatus used is an automatic KRUSS tensiometer equipped with a K121 adsorption software. The measurements are performed at 25° C.

The detergent according to the invention thus impregnates the washing better than previous detergents, during a wash of several tens of minutes.

Measurement of the wetting angles is performed by means of the KRUSS tensiometer equipped with the "K121 Contact Angle" software against a polyethylene plate 2 cm in length.

This software permits continuous recording of the weight of polyethylene during its 5-min penetration into the surfactant solution. The angle of contact during the forward movement is determined by mathematical extrapolation at the origin.

The results confirm the usefulness of alkyl galactoside uronates in the detergents sector, especially for alkyl chains having up to 14 carbon atoms. Sodium decyl galactoside uronate whose wetting angle (3°) is considerably less than that of sodium lauryl sulphate (70°), sodium lauryl ether sulphate containing two moles of ethylene oxide (60°) and sodium dodecylbenzenesulphonate (38°), is preferred. Here again, these values show that the detergent according to the invention impregnates the washing better than previous detergents.

The prepared alkyl galactoside uronates very effectively reduce the surface tension of the water. This property was determined by the usual tensiometric technique using a type K12 KRUSS tensiometer and according to the ISO 304 standard. The measurement is performed at 25° C. The mobile measurement device is a rectangular platinum foil (25 mm×5 mm).

The completely automatic apparatus makes it possible to perform repetitive measurements and calculate the statistical mean of 10 values.

When R1 has less than 12 carbon atoms, this reduction in surface tension is greater than that observed with known products (sodium lauryl sulphate, sodium lauryl ether sulphate containing 2 moles of ethylene oxide, sodium dodecylbenzenesulphonate, alkyl glucoside, alkyl polyglucosides and the like); it is the same when R1 has more than 12 carbon atoms. Emulsification of the dirt present in the washing is thus made easier.

All these properties (foaming power, wettability, wetting angle, reduction of surface tension and the like) mean that alkyl galactoside uronates can in particular be used as detergents (especially in the laundry soap sector). Sodium alkyl galactoside uronates especially, having 8 to 14, particularly 8 to 12, and more particularly 10 carbon atoms in their alkyl chain, are preferred.

The subject of the invention is also a process for imparting surfactant properties to a composition, characterised in that it consists in incorporating therein 0.1 to 60% by weight of a derivative or a mixture of derivatives according to the invention.

A powdered detergent composition according to the invention contains 0.1 to 60%, and preferably 10 to 30% by weight of a detergent base and 99.9 to 40%, and preferably 90 to 70% by weight of adjuvants.

The detergent base may be a derivative or a mixture of derivatives according to the invention. It can also be a mixture of one or more derivatives according to the invention with one or more conventional surfactants in the sector, it being possible for these surfactants to be anionic, nonionic, cationic or amphoteric. The proportion of surfactants according to the invention represents 1 to 100% by weight, and preferably 50 to 100% of the total surfactant content.

The anionic surfactants of the composition, other than those of the invention, may be alkyl benzenesulphonates, fatty alcohol sulphates, fatty alcohol ether sulphates or α-olefinsulphonates, and among those relating to the invention, those for which R1 is an alkyl having 8 to 14 carbon atoms, will be preferred. The total anionic surfactants of the composition represent 30% to 90% by weight, and preferably 40 to 70% by weight of the total surfactant content. The nonionic surfactants of the composition, when they are different from those of the invention, may be in particular alkyl poly(ethylene glycol) ethers and nonylphenyl poly(ethylene glycol) ethers, and when they are those of the invention, are alkyl galactoside uronates preferably of 6 to 12 carbon atoms per alkyl chain.

The adjuvants are "builders", bleaching agents and various additives such as antiredeposition agents, anticorrosive agents, enzymes, optical whiteners, exhausting agents or foam regulators, colorants, perfumes, opacifiers and the like.

The builders may be a phosphate salt, especially a triphosphate salt for example of an alkali metal, and in particular of sodium, nitrilotriacetic acid or its salts of alkali metals, especially sodium, citric acid or its salts, especially of alkali metals, especially of sodium, a glyconic acid, especially gluconic acid or galactonic acid and its salts, especially of an alkali metal, and in particular of sodium, a carbonate salt of an alkali metal, especially of sodium, a polyacrylic acid or its salts, especially of an alkali metal.

These builders may be used mixed in various proportions. The ratio of the total builder content to that of the total surfactant base is between 1 and 4, preferably between 2 and 3.

The bleaching agents may be a perborate salt, especially of an alkali metal, and in particular of sodium, a percarbonate salt especially of an alkali metal, and in particular of sodium, and may or may not contain a bleaching activator, especially tetraacetylglycolurile, 1,5-diacetyl-2,4-dioxohexahydro-1,3,5-triazine, tetraacetylethylenediamine, N,N-diacetyl-N,N'-dimethylurea, polyacetate salts of carbohydrates, in particular of hexoses or of pentoses, and more particularly of glucose or sucrose, or a bleaching stabilizer chosen from the usual stabilizers, especially ethylenediaminetetraacetate (EDTA) or phosphonates. These bleaching agents represent 0.2 to 25% by weight of the powdered detergent composition.

The antiredeposition agents may be cellulose ethers, especially carboxymethylcellulose, and their salts of alkali metals, especially of sodium, or the usual synthetic polymers in this type of formulation. They represent 0.5 to 3%, and preferably 0.5 to 2% by weight of the detergent composition. The anticorrosive agent may be a silicate salt of an alkali metal, especially of sodium, whose proportion represents 0.5 to 25% by weight of the detergent composition.

The enzymes are especially proteases or amylases. The optical whiteners are those conventionally used in the sector, especially stilbenedisulphonic acid or bis(styryl)biphenyl derivatives. The foam exhausting agents may be alkyl ethanolamide, especially cocomonoethanolamide. The foam regulators may be especially silicones, soaps or paraffins.

The powdered detergent composition is used at a concentration of 1 to 20 g/l, and preferably between 1 and 6 g/l. The washing is carried out in a conventional machine between 20° and 80° C., and preferably between 20° and 60° C., for a period of 10 to 60 minutes.

A liquid detergent composition according to the invention contains 0.1 to 60%, and preferably 10 to 60% by weight of a detergent base, 99.9 to 40%, and preferably 90 to 70% by weight of adjuvants.

The detergent base may be a derivative or a mixture of derivatives according to the invention. It can also be a mixture of one or more derivatives according to the invention with one or more conventional surfactants in the sector; these surfactants may be anionic, nonionic, cationic or amphoteric. The proportion of surfactants according to the invention represents 1 to 100% by weight, and preferably 50 to 100% by weight of the total surfactant content. The anionic surfactants used, when they are different from those of the invention, may be in particular an alkyl benzene sulphonate, a soap or a fatty alcohol sulphate ether. The nonionic surfactants used, when they are different from those of the invention, may be in particular alkyl poly (ethylene glycol) ethers, and when they are those of the invention, alkyl alkyl galactoside uronates in particular with an alkyl having 6 to 14 carbon atoms. When a cationic surfactant is incorporated into the formulation, it may be a dialkyldimethylammonium chloride.

Conventional ingredients make up the formulation; these are in particular foam exhausting agents (0–2%), enzymes, in particular proteases (0–2%), builders (0–30% and preferably 10 to 30%), in particular sodium citrate or sodium silicate, zeolites or polycarboxylates, stabilizers, in particular tri- and monoethanolamine and chelating agents, solubilization solvents (5–15%), in particular ethanol or propylene glycol (5–15%), optical whiteners, clays, perfumes, colorants and water (30–60%).

The subject of the invention is also the use of the derivatives according to the invention for producing a detergent composition for dish washing and for domestic uses. This composition contains 1 to 30% by weight, and preferably 5 to 25% of derivatives according to the invention, and 99.9 to 70% by weight, and preferably 95 to 75% of adjuvants. These adjuvants may be other anionic surfactants, in particular an ethoxylated fatty alcohol sulphate (0–20% by weight), a thickener, in particular sodium chloride (0–5%), an ethoxylated or nonethoxylated fatty acid mono or triethanolamide (0–15%), a sodium polyacrylate (0–5% by weight), a calcium-complexing agent, in particular EDTA (0–5%), a solvent, in particular ethanol (0–5%), a fatty amine oxide (0–10%), a perfume, a colorant, a preservative and the like, in sufficient amounts.

The compositions according to the invention have a pleasant feel and are easily rinsed.

The liquid detergent composition according to the invention is used in aqueous solution at a concentration of 6 to 12 g/l, and at temperatures of 40° to 70° C.

The subject of the invention is also cosmetic compositions containing 0.1 to 50%, and preferably 5 to 35% by weight of active substance, and 99.9 to 50%, and preferably 95 to 65% by weight of excipients, characterized in that the detergent or emollient is a derivative of formula I according to the invention. Octadecyl, hexadecyl and tetradecyl galactoside uronates are preferred because of their low critical micelle concentration (0.3 to 1.2 g/l) and because of their lower aggressiveness towards the mucous membranes and the skin (Lang G. and Spengler L., Prepurits. IF SCC Congr., 1986, Vol. I, p. 25). In particular, sodium decyl and dodecyl galactoside uronates will be preferred for their good foaming power.

The cosmetic composition may be a gentle liquid soap containing 5 to 30% by weight, and preferably 5 to 20% of a derivative according to the invention, and 95 to 70% by weight, and preferably 95 to 80% by weight of excipients. These excipients may be another anionic surfactant, in particular sodium cocoyl isethionate (0–10% by weight), Na lauryl sulphate (0–10%), the sodium salt of an alkyl peptide (0–15% by weight), an amphoteric surfactant, in particular an alkyl amidopropylbetaine such as cocoamidopropylbetaine (0–10% by weight), a heavy mineral oil (0–20% by weight), a cellulose derivative, in particular a carboxymethylcellulose (0–1%), a solvent, in particular an alcohol such as ethanol or propylene glycol (0–5% by weight), a complexing agent, in particular EDTA (0–2%), sodium chloride (qs), a fatty alcohol, in particular cetyl alcohol (0–5% by weight), preservatives, perfumes and colorants (qs).

The cosmetic composition may be a shampoo, in particular a gentle shampoo for frequent use. It is composed of 5 to 35% by weight of a detergent base, preferably 10 to 75% of which consists of a derivative or a mixture of derivatives according to the invention, and 95 to 65% of adjuvants.

The other surfactants which constitute the detergent base may be an alkyl ether sulphate such as sodium or magnesium lauryl ether sulphate, a polyoxyethylenated sodium alkyl ether sulphate such as polyoxyethylenated sodium lauryl ether sulphate, an alkyl betaine such as cocoyl betaine, an alkyl amidopropylbetaine such as cocoyl amidopropylbetaine, an alkyl dimethylaminoacetic acid betaine such as lauryl dimethylaminoacetic acid betaine, an alkyl dimethylamino hydroxypropyl sulphobetaine, a sodium α-olefinsulphonate, an alkyl polyethylene glycol such as octadecyl PEG 15, an alkyl imidazoliniumbetaine such as cocoyl imidazolinium betaine, an alkyl ether sulphosuccinate such as disodium lauryl ether sulphosuccinate, a β-alkyl aminopropionate such as sodium β-lauryl aminopropionate, an alkyl diaminoethylglycine such as sodium lauryl diaminoethylglycine and, when they are derivatives according to the invention, they are preferably alkyl galactoside uronates with the alkyl having 10 to 14 carbon atoms.

The adjuvants may be thickeners, texturing agents such as fatty acid diethanolamides, in particular cocoyl diethanolamide such as an alkyl acrylate, in particular lauryl acrylate, sodium chloride, ethylene glycol dialkylcarboxylate such as ethylene glycol distearate, a fatty amine N-oxide such as N-cocoyl oxide and the like, which are incorporated into the formulation in an amount of 0–10% by weight. The adjuvants may also be conditioning agents, emollients such as wheat protein hydrolyzates, such as cellulose ethers containing quaternary ammonium salts (nitrogen content of 1–3%, MW=50-150 000), an acrylamide/dimethylalkylammonium chloride copolymer, representing 0.5 to 5% by weight of the formulation, complexing agents, in particular EDTA or galactaric acid representing 0.1 to 1% by weight of the formulation, and finally perfumes, pearling agents, preservatives, a sufficient amount of acidifiers, and purified water.

The cosmetic composition may be a bath foam containing 5 to 35% of a detergent base, itself consisting of more than 50% of derivatives or a mixture of derivatives according to the invention, and adjuvants. The other constituents of the detergent base are conventional compounds in the sector and may be in particular alkyl amidobetaines such as cocoyl amidopropylbetaine, an ethoxylated sorbitan alkyl carboxylate such as an ethoxylated sorbitan laurate.

The adjuvants are fatty acid mono- or triethanolamides (0–10% by weight), an ethoxylated propylene glycol dialkylcarboxylate (0–5% by weight), a polyethylene glycol, in particular triethylene glycol (0–5% by weight), an alkyl acrylic, in particular an oleyl acrylic (0–5% by weight), a vegetable oil, in particular sweet almond oil (0–10% by weight), sodium chloride (qs), EDTA (0–0.5% by weight), a fatty alcohol, in particular hexadecanol (0–2% by weight), a preservative, a perfume, a sufficient amount of colorant, and water.

The cosmetic composition may be a shower gel containing 5 to 35% of a detergent base, itself consisting of not less than 50% of derivatives or a mixture of derivatives according to the invention, and adjuvants.

The surfactants which are capable of making up the detergent base, when they are not those of the invention, may be a polyoxyethylenated alkyl sulphosuccinate such as cocoyl sulphosuccinate containing 3 moles of ethylene oxide, an alkyl amino-N-glycinate such as C12–C18 amino-N-glycinate, an ammonium alkyl sulphate such as ammonium lauryl sulphate.

The adjuvants may be an ethoxylated propylene glycol alkylcarboxylate such as ethoxylated propylene glycol dioleate (0–5% by weight), an alkyl amidobetaine such as a lauryl amidopropylbetaine (0–5% by weight), a pearling agent (0–7% by weight), an acrylic gel (0–1% by weight), sodium chloride, a complexing agent, a preservative, a sufficient amount of perfume, and purified water.

The cosmetic composition may also be a composition of the toothpaste, mouthwash, syndet type and the like.

The cosmetic composition may be, in particular by incorporation of alkyl alkyl galactoside uronate according to the invention, octyl octyl galactoside uronate, in particular which forms a gel type structure for water concentrations greater than 60%, and preferably greater than 90%, a face cream in particular.

The derivatives according to the invention are also extrinsic liquid crystals, in particular hexyl hexyl D-galactoside uronate and octyl octyl D-galactoside uronate when they are at concentrations of between 5 and 60% by weight, in particular in water.

These alkyl galactoside uronic acids, their esters and their salts may be prepared by a process which consists in reacting an alcohol of formula R1OH with the galacturonic acid of formula:

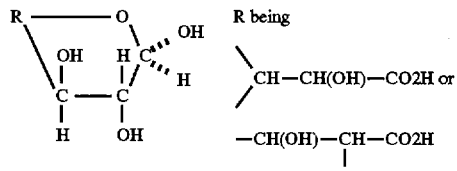

for which the carbon carrying the hydroxyl group is not attached to the endocyclic oxygen atom, to give a mixture of alkyl alkyl galactoside uronates of formula

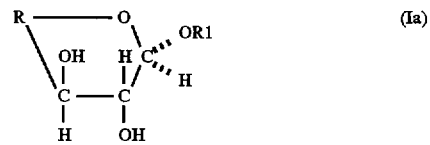

in which R2 is R1 and R has the two meanings indicated, and in separating each alkyl alkyl galactoside uronate from the mixture, and to give the derivatives (I) in which R2 is an alkali metal, an alkaline-earth metal or a quaternary ammonium group, in salifying a derivative of formula (Ia) by a base of formula Me(OH)$_x$ in which Me is an alkali metal, an alkaline-earth metal or

x being the valency of the metal or being equal to 1 when Me is

and to give the derivatives (I) in which R2 is hydrogen, in acidifying the derivatives (I), in which R2 is a metal or a quaternary ammonium group, with an acid.

Galacturonic acid may be prepared by hyrolyzing pectins (Anderson King J., J. Chem. Soc., 1961, page 5333).

Unlike the prior art, which requires the reaction of an acid or a lower ester with a sugar having a certain number of hydroxyls on each of which the acid or ester reacts with formation of as many side chains, the process according to the invention involves the reaction of an alcohol with a sugar possessing, in addition to an appropriate anomeric alcohol functional group, namely the alcohol functional group carried by the carbon in the alpha position relative to the endocyclic oxygen, a carboxylic acid functional group, such that the reaction of the alcohol occurs exclusively at these two positions, which gives a perfect regioselectivity with only two side chains at well-defined positions.

Moreover, as the esterification reaction (on the carboxylic acid functional group) is more rapid than that of glycosidation (on the anomeric alcohol functional group), the starting sugar or substrate, which is initially of low solubility in the reaction medium consisting of alcohol optionally supplemented with a solvent, rapidly takes on a lipophilic character which makes it more soluble and promotes the glycosidation reaction, which can from then on occur more rapidly under gentler conditions, thus resulting in a lesser coloration of the product obtained while having a high yield.

In practice, the process consists

For preparing alkyl alkyl galactoside uronates:
in bringing into contact one equivalent of galacturonic acid;

2 to 50 molar equivalents, and preferably 2 to 10 molar equivalents of an alcohol of formula R1OH;

$10^{-3}$ to 1, and preferably $10^{-2}$ to $10^{-1}$ molar equivalent of an acid catalyst such as hydrochloric acid, sulphuric acid, an alkyl sulphuric acid such as decyl or lauryl sulphuric acid, a sulphonic acid such as benzenesulphonic acid, para-toluenesulphonic acid, camphorsulphonic acid, an alkylsulphonic acid such as methylsulphonic acid, decylsulphonic acid, laurylsulphonic acid, sulphosuccinic acid or an alkyl sulphosuccinate such as decyl sulphosuccinate or lauryl sulphosuccinate, perhalohydric acids such as perchloric acid, metals such as copper or iron, their oxides or their salts such as their halides, halogens such as iodine, antimony pentahalides, especially pentachlorides or pentafluorides, or titanium sulphates.

This acid catalysis may also be performed using 0.05 to 6 equivalents by weight of a sulphonic resin in its $H^+$ form, or of an acidic clay. When the dehydrating effect of the resin is used, resins with a high water retention capacity are preferred for this heterogeneous catalysis.

Sulphuric acid, alkyl sulphuric acid, methanesulphonic acid, alkylsulphonic acid, succinic acid or an alkyl succinate, iodine or a sulphonic resin are preferred.

2 to 20 equivalents by weight, relative to the substrate, of a solvent which may be an ether oxide such as tetrahydrofuran, dioxane, ethylene glycol dimethyl ether, diethylene glycol dimethyl ether, a halogenated hydrocarbon such as dichloromethane, chloroform or dichloroethane, an ester such as ethyl acetate, propyl acetate or butyl acetate, a nitrated solvent such as nitromethane, nitroethane or 2-nitropropane, a solvent of the family of amides such as N-methylformamide, N,N-dimethylformamide, N,N-dimethylacetamide or N-methyl-2-pyrrolidone, a nitrile such as acetonitrile or an alkane, preferably hexane, heptane or octane, or an aromatic solvent such as toluene or xylene.

A mixture of two or more of these solvents may also be used or the reaction performed in the complete absence of a solvent.

A conventional dehydrating agent such as molecular sieves or zeolites, whether they are directly added to the reaction medium or the reaction filtrate is circulated through a thermostatted column filled with this dehydrating agent, may be used.

In performing the reaction at temperatures of between 25° and 140° C., and preferably between 50° C. and 90° C., and for a period of 1 hour to 3 days, and preferably 3 hours to 24 hours;

In carrying out the reaction at a pressure of between 0.1 and 760 mmHg, and preferably between 0.1 mm and 300 mmHg;

In filtering the acid catalyst during heterogeneous catalysis, or in neutralizing the acid catalyst, and then in filtering its salt during homogeneous catalysis. Neutralization of the reaction medium is carried out for example using an alkali metal hydrogen carbonate, especially sodium hydrogen carbonate;

In evaporating the solvent and/or excess alcohol R1OH in order to recover the mixture of alkyl alkyl galactoside uronates of formula I;

In chromatographing the mixture of these alkyl alkyl galactoside uronates on a silica column in order to separate them.

For preparing the alkyl galactoside uronic acid salts:
in bringing into contact one equivalent of alkyl alkyl galactoside uronates, 0.1 to 20 equivalents by weight of a solvent which may be water, an alkane, preferably pentane, hexane, heptane or octane, an ether oxide such as tetrahydrofuran, dioxane, ethylene glycol dimethyl ether or diethylene glycol dimethyl ether, a halogenated hydrocarbon such as dichloromethane, chloroform or dichloroethane, an alcohol which may be in particular an alcohol with a short carbon chain such as methanol, ethanol, propanol, isopropanol or butanol, or with a longer carbon chain, especially such as octanol, decanol, dodecanol, tetradecanol and the like.

A mixture of two or more of these solvents may also be used or the reaction performed in the complete absence of a solvent.

Water, methanol, ethanol, isopropanol, tetrahydrofuran, pentane, hexane and heptane are preferred.

0.5 to 10, and preferably 1 to 3 equivalents of a base of formula

Me(OH)$_x$ in which Me is an alkali metal or an alkaline-earth metal or

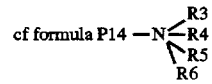

x being the valency of the metal or equal to 1 when Me is (formula P14)

Sodium hydroxide, potassium hydroxide, ammonium hydroxide or alkyl(hydroxyalkyl)ammonium hydroxide are preferred.

Optionally, $10^{-1}$ to $10^{-3}$ and preferably $10^{-1}$ to $10^{-2}$ of a phase transfer catalyst, for example a nonionic, cationic or anionic surface-active agent among which hexadecyltrimethylammonium chloride is most particularly preferred. Tetrabutylammonium chloride, benzyltrimethylammonium chloride, oleylamine, triacetylmethylammonium chloride, tricaprylmethylammonium chloride, tetrabutylammonium acid sulphate and, in addition to these ammonium and amine ions, phosphonium ions, crown ether oxides, ethoxylated alcohols, cryptands, amino polyethers, phosphoryl sulphoxides, certain natural ionophores, glycerol esters, sorbitan esters and the like may also be used.

The reaction is preferably performed without a phase transfer catalyst.

In performing the reaction at temperatures of between 0° C. and 100° C., and preferably between 0° C. and 60° C., and for a period of 15 min to 360 min, and preferably 15 min to 120 min.

In removing the alcohol R1OH, the solvent or solvent system used, by filtration or evaporation.

In recovering, washing with a solvent or a mixture of solvents chosen from the list of reaction solvents and then drying the alkyl galactoside uronic acid salts obtained.

In optionally taking up these alkyl galactoside uronic acid salts with 0.5 to 50, and preferably 1 to 5 equivalents of water, and in decolorizing the solution obtained on activated carbon or on an adsorbent resin.

In filtering the activated carbon or the resin in order to recover the decolorized alkyl galactoside uronic acid salts. And for preparing the alkyl galactoside uronic acids:

Acidifying the alkyl galactoside uronic acid salts with one equivalent or more of an acid such as hydrochloric acid, sulphuric acid, a sulphonic acid or a sulphonic resin in its $H^+$ form.

The following examples illustrate the invention:

1) EXAMPLE NO. 1

Preparation of ethyl ethyl D-galactoside uronate: (I, R1=R2=ethyl)

10 g of previously dried Amberlyst 15 sulphonic resin are added to 10 g (47.1 mmol) of D-galacturonic acid monohydrate suspended in 100 ml (79 g, 1714.7 mmol) of absolute ethanol. The reaction mixture is heated at 80° C. for 8 hours and then filtered. After passing over activated carbon, filtering again and concentrating the filtrate under vacuum, 10.6 g (90% yield) of a clear, slightly yellowish oil are obtained corresponding to ethyl ethyl D-galactoside uronate which is predominantly present in its β-furanose form, the other forms being, in decreasing order of abundance, α-pyranose, α-furanose and β-pyranose.

Flash chromatography of the crude product on a silica column (35 to 70 μm), using ethyl acetate as mobile phase, makes it possible to isolate each of the four isomers formed, whose physicochemical characteristics are summarised below.

Rf using thin-layer chromatography:

Silica plate with a film thickness of 200 μm and a particle size of 5 to 10 μm, using ethyl acetate as migration solvent.

|  | Rf |
|---|---|
| β-furanose | 0.47 |
| α-furanose | 0.41 |
| β-pyranose | 0.19 |
| α-pyranose | 0.15 |

2) EXAMPLE NO. 2

Preparation of butyl butyl D-galactoside uronate (I, R1=R2=butyl)

0.4 ml (0.73 g; 7.06 mmol) of concentrated sulphuric acid is added to 25 g (117.8 mmol) of D-galacturonic acid monohydrate suspended in 230 ml (186 g, 2510 mmol) of n-butanol and then the reaction mixture is heated to 80° C.

After reacting for 3 hours, the solution is cooled, neutralized with excess sodium hydrogen carbonate and filtered, and the filtrate is treated with activated carbon. After filtering again, the filtrate obtained is concentrated under vacuum to give 33.5 g (93% yield) of a clear, light yellow oil corresponding to butyl butyl D-galactoside uronate whose four isomeric forms can be separated under the following conditions:

Flash chromatography of the crude product obtained on a silica column which is identical in nature to that described in Example No. 1 and using, in the first instance, the eluent system ethyl acetate/hexane −70/30 by volume in order to separate the β-furanose and α-furanose forms, and then ethyl acetate in order to separate the β-pyranose and then α-pyranose forms, whose physico-chemical characteristics, obtained by thin-layer chromatography performed under the conditions described in Example No. 1, are described below.

|  | Rf |
|---|---|
| β-furanose | 0.61 |
| α-furanose | 0.61 |
| β-pyranose | 0.45 |
| α-pyranose | 0.36 |

| $^{13}$C NMR in CDCl$_3$ | | | | | | |
|---|---|---|---|---|---|---|
|  | C1 | C2 | C3 | C4 | C5 | C6 |
| β-furanose | 107.80 | 80.20 | 77.17 | 85.22 | 69.53 | 172.22 |
| α-furanose | 100.83 | 77.52 | 74.24 | 82.61 | 69.74 | 172.10 |
| β-pyranose | 107.89 | 70.59 | 73.09 | 69.95 | 73.97 | 168.26 |
| α-pyranose | 98.85 | 68.12 | 69.83 | 70.22 | 70.40 | 169.04 | with, for the pyranose forms, the following $^{13}$C shifts for the "butyl" groups:

| $^{13}$C MR in D$_2$O: the table below gives the chemical shifts in ppm. | | | | | | | | | | | |
|---|---|---|---|---|---|---|---|---|---|---|---|
|  | $C_1$ | $C_2$ | $C_3$ | $C_4$ | $C_5$ | $C_6$ | O—CH$_2$—CH$_3$ | CO$_2$—CH$_2$—CH$_3$ | O—CH$_2$—CH$_3$ | CO$_2$—CH$_2$—CH$_3$ | |
| β-furanose | 109.98 | 83.69 | 78.62 | 86.00 | 72.15 | 176.16 | 67.14 | 65.53 | 17.35 | 16.38 | |
| α-furanose | 103.57 | 78.90 | 76.42 | 84.79 | 73.47 | 176.05 | 67.52 | 65.59 | 17.10 | 16.20 | |
| β-pyranose | 105.11 | 73.02 | 75.24 | 72.60 | 77.02 | 172.88 | 67.05 | 65.44 | 17.26 | 16.34 | |
| α-pyranose | 106.16 | 70.51 | 71.81 | 73.00 | 73.49 | 173.64 | 67.31 | 65.49 | 17.01 | 16.26 | |

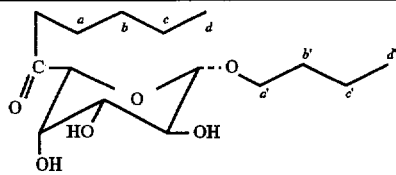

formula P21

| β$^{13}$C of the compounds | a | a' | b | b' | c | c' | d | d' |
|---|---|---|---|---|---|---|---|---|
| β-pyranose | 65.30 | 70.06 | 30.41 | 31.42 | 18.92 | 18.92 | 13.54 | 13.74 |
| α-pyranose | 65.04 | 68.38 | 31.30 | 30.3 | 19.01 | 18.77 | 13.55 | 13.39 |

3) EXAMPLE NO. 3

Preparation of n-hexyl n-hexyl D-galactoside uronate: (I/R1=R2=n-hexyl)

11.8 ml (9.6 g; 94.2 mmol) of n-hexanol and 2 ml (23.60 g; 35.3 mmol) of concentrated sulphuric acid are added to 10 g (47.1 mmol) of D-galacturonic acid monohydrate. The reaction mixture is heated and then kept at 60° C. for 24 hours. The residue is taken up with 50 ml of ethyl acetate and excess sodium hydrogen carbonate is added, the mixture is filtered and the filtrate is treated with activated carbon. After filtering again, the mixture is concentrated under vacuum to give 13.7 g (80% yield) of n-hexyl n-hexyl D-galactoside uronate in the form of a clear yellow oil. Flash chromatography performed under the conditions of Example No. 1 makes it possible to isolate its 4 isomeric forms. They have the following physicochemical characteristics.

TLC performed under the conditions of Example No. 2:

| COMPOUND | Rf |
|---|---|
| α-furanose | 0.68 |
| β-furanose | 0.63 |
| β-pyranose | 0.46 |
| α-pyranose | 0.36 |

$^{13}$C NMR in CDCl$_3$:

| | C1 | C2 | C3 | C4 | C5 | C6 |
|---|---|---|---|---|---|---|
| β-furanose | 107.90 | 80.17 | 77.90 | 85.35 | 69.58 | 171.97 |
| α-furanose | 100.89 | 77.25 | 74.25 | 82.75 | 69.77 | 170.90 |
| β-pyranose | 102.87 | 77.66 | 73.06 | 69.89 | 73.91 | 168.22 |
| α-pyranose | 98.85 | 68.36 | 70.08 | 70.27 | 70.41 | 169.03 |

4) EXAMPLE NO. 4

Preparation of n-octyl n-octyl D-galactoside uronate (R1:R2:n-octyl)

600 ml (494 g; 3.80 moles) of n-octyl and 30 g of S 100 resin from Bayer (gel type) are added to 50 g (0.235 mole) of D-galacturonic acid monohydrate. The mixture is heated to 80° C. and after reacting for 30 hours, the resin is filtered and the filtrate is treated with activated carbon and concentrated under vacuum created by means of a slide vane rotary vacuum pump (temperature of 73° C. and a vacuum of 145 mPa) to give 90.7 g (92% yield of n-octyl n-octyl D-galactoside uronate in the form of an orange-colored oil. Flash chromatography performed under the same conditions as in Example 1 makes it possible to isolate its four isomeric forms whose physicochemical characteristics are given below.

TLC performed under the conditions of Example No. 2.

| COMPOUND | Rf |
|---|---|
| α-furanose | 0.72 |
| β-furanose | 0.66 |
| β-pyranose | 0.52 |
| α-pyranose | 0.42 |

$^{13}$C NMR in CDCl$_3$:

| | C1 | C2 | C3 | C4 | C5 | C6 |
|---|---|---|---|---|---|---|
| β-furanose | 107.95 | 80.30 | 77.16 | 85.31 | 69.58 | 171.97 |
| α-furanose | 100.93 | 77.79 | 74.58 | 82.83 | 69.82 | 167.51 |
| β-pyranose | 102.90 | 70.68 | 73.09 | 69.91 | 74.01 | 167.60 |
| α-pyranose | 98.96 | 68.18 | 69.87 | 70.30 | 70.42 | 167.25 |

5) EXAMPLE NO. 5

Preparation of n-decyl n-decyl D-galactoside (I/R1=R2=n-decyl).

1000 ml (829 g; 5.237 moles) of n-decyl and 5 g (26.28 mmol) of para-toluenesulphonic acid monohydrate are added to 200 g (0.940 mole) of D-galacturonic acid monohydrate. The mixture is heated to 60° C. under a vacuum 260 mm of mercury, for 24 hours. After distillation of the excess n-decanol, 473 g of a clear yellowish oil are recovered containing about 50 g of residual n-decanol. Yield of n-decyl n-decyl galactoside uronate: 473 g (95%).

Chromatography on a silica gel column (35 to 70 μm), using as eluent a petroleum ether/ethyl ether system (1.1, v/v), and then ethyl ether, and finally an ethyl ether/ethyl acetate system (6/4 - v/v), makes it possible to separate the 4 isomers formed. The α-pyranose, β-pyranose and β-furanose isomers crystallize after evaporation of the elution solvent. They are then recrystallized.

The α-furanose isomer remains in the form of an oil

| | *Rf | Melting point | Recrystallization solvent | Infrared U:cm$^{-1}$ c = O | -0-4 |
|---|---|---|---|---|---|
| α-furanose | 0.48 | "oil" | " | | |
| β-furanose | 0.45 | 57–58° C. | ethyl ether/ petroleum ether | 1730 | 3400 |
| β-pyranose | 0.37 | 127–128° C. | dichloromethane/ ethyl ether | 1720 | 3400 |
| α-pyranose | 0.32 | 75–77° C. | dichloromethane/ ethyl ether | 1760 | 3400 |

*TLC performed with the eluent system "dichloromethane-methanol 95–05/ v–v

| ¹³C MR in D₂₀: the table below gives the chemical shifts in ppm. | | | | | | | | | | |
|---|---|---|---|---|---|---|---|---|---|---|
| | $C_1$ | $C_2$ | $C_3$ | $C_4$ | $C_5$ | $C_6$ | O—$\underline{CH_2}$—CH₃ | CO₂—$\underline{CH_2}$—CH₃ | O—CH₂—$\underline{CH_3}$ | CO₂—CH₂—$\underline{CH_3}$ |
| β-furanose | 109.98 | 83.69 | 78.62 | 86.00 | 72.15 | 176.16 | 67.14 | 65.53 | 17.35 | 16.38 |
| α-furanose | 103.57 | 78.90 | 76.42 | 84.79 | 73.47 | 176.05 | 67.52 | 65.59 | 17.10 | 16.20 |
| β-pyranose | 105.11 | 73.02 | 75.24 | 72.60 | 77.02 | 172.88 | 67.05 | 65.44 | 17.26 | 16.34 |
| α-pyranose | 106.16 | 70.51 | 71.81 | 73.00 | 73.49 | 173.64 | 67.31 | 65.49 | 17.01 | 16.26 |

| ¹³C NMR in CDCl₃ | | | | | | | | | | |
|---|---|---|---|---|---|---|---|---|---|---|
| | $C_1$ | $C_2$ | $C_3$ | $C_4$ | $C_5$ | $C_6$ | —O—$\underline{CH_2}$ | CH₃ | CO₂CH₂— | $(\underline{CH_2})_8$CH₃ |
| α-furanose | 100.94 | 78.16 | 75.66 | 82.82 | 70.00 | 172.31 | 69.41 | 14.10 | 65.97 | 22.71; 25.90; 26.07; 28.61; 29.34; 29.62; 31.92; |
| β-furanose | 108.33 | 79.32 | 77.86 | 86.66 | 70.08 | 172.12 | 67.86 | 14.07 | 66.37 | 22.68; 25.90; 26.15; 28.59; 29.32; 29.43; 29.56; 31.89; |
| β-pyranose | 103.05 | 70.90 | 73.28 | 70.57 | 74.15 | 168.25 | 70.06 | 14.13 | 65.80 | 22.71; 25.96; 28.59; 29.40; 29.62; 31.97 |
| α-pyranose | 98.90 | 68.73 | | 70.44 | | 169.06 | 69.08 | 14.07 | 65.75 | 22.68; 25.82; 26.10; 28.56; 29.40; 29.62; 31.89; |

6) EXAMPLE NO. 6

Preparation of n-dodecyl n-dodecyl D-galactoside uronate (I/R1=R2=dodecyl)

Method A 800 ml of diglyme, 702 g (3.77 moles) of n-dodecanol and 7.36 g (0.08 mole) of concentrated sulphuric acid are added to 200 g (0.94 mole) of D-galacturonic acid monohydrate. The mixture is heated to 60° C. under a vacuum of 18 mm of mercury for 24 hours. The mixture is adjusted to pH=7 with sodium hydrogen carbonate. The salts formed are filtered and the filtrate is concentrated. After chromatography on silica gel, the predominant n-dodecyl n-dodecyl D-galactoside uronate isomers are recovered with an overall yield of 70% (same eluent system as in Example No. 6).

| | *Rf | Melting point | Recrystallization solvent | Infrared U:cm⁻¹ | |
|---|---|---|---|---|---|
| | | | | c = H | —O—H |
| β-furanose | 0.47 | 71–72° C. | ethyl ether | 1730 | 3400 |
| β-pyranose | 0.36 | 127–128° C. | ethyl acetate | 1720 | 3400 |
| α-pyranose | 0.31 | 83–84° C. | ethyl acetate | 1760 | 3400 |

*same eluent system as in Example No. 5

| ¹³C NMR in CDCl₃ | | | | | | | | | | |
|---|---|---|---|---|---|---|---|---|---|---|
| | $C_1$ | $C_2$ | $C_3$ | $C_4$ | $C_5$ | $C_6$ | —O—$\underline{CH_2}$ | CH₃ | —CO₂CH₂— | $(\underline{CH_2})_{10}$CH₃ |
| β-furanose | 108.53 | 78.71 | 78.14 | 87.31 | 70.24 | 172.06 | 67.85 | 14.12 | 66.65 | 22.71; 25.79; 26.17; 28.60; 29.27; 29.39; 29.52; 29.58; 29.63; 29.67; 29.70; 31.95; |
| β-pyranose | 103.02 | 71.06 | 73.25 | 70.63 | 74.12 | 168.22 | 70.00 | 14.18 | 65.89 | 22.76; 26.01; 26.41; 29.43; 29.75; 31.00; |
| α-pyranose | 98.81 | 69.00 | 70.33 | 70.63 | | 168.95 | 69.14 | 14.06 | 65.78 | 22.67; 25.82; 26.10; 28.57; 29.26; 29.35; 29.43; 29.50; 29.54; 29.60; 29.65; 31.93; |

Method B

Performed with the same amounts of D-galacturonic acid and fatty alcohol as in method A, but using as acid catalyst 4 g of sulphosuccinic acid, and carrying out the reaction at 70° C. under a vacuum of 60 mm of mercury. After reacting for 12 hours, the reaction mixture is chromatographed on a silica gel (same elution systems as in Example No. 6). The predominant isomers of n-dodecyl dodecyl D-galactoside uronate described above are recovered with an overall yield of 80%.

7) EXAMPLE NO. 7

Preparation of n-tetradecyl n-tetradecyl galactoside uronate (I/R1=R2=n-tetradecyl)

Prepared according to Example 7, method B, with an overall yield of 85%. The acid catalyst used is para-toluenesulphonic acid monohydrate (5 g). (see tables pages 35–36).

8) EXAMPLE NO. 8

Preparation of n-hexadecyl n-hexadecyl galactoside uronate (I/R1=R2=n-tetradecyl)

Prepared according to Example 7, method B, with an overall yield of 90%, but the acid catalyst used is para-toluenesulphonic acid (6 g) and the elution system for the chromatographic purification is as follows: dichloromethane until excess n-hexadecanol comes out, and then the dichloromethane/methanol system (98/02-v/v). The 4 isomers isolated crystallize after evaporation of the elution solvents and they are then recrystallized. (See tables pages 37–38).

|  | *Rf | Melting point | Recrystallization solvent | Infrared U:cm$^{-1}$ c = O | —O—H |
|---|---|---|---|---|---|
| β-furanoside | 0.47 | 77–79° C. | ethyl ether | 1730 | 3400 |
| β-pyranoside | 0.37 | 125–126° C. | ethyl acetate | 1720 | 3400 |
| α-pyranoside | 0.33 | 89–91° C. | dichloromethane/ isopropyl ether | 1760 | 3400 |

*TLC performed with the same solvent system as in Example No. 5

|  | *Rf | Melting point | Recrystallization solvent | Infrared U:cm$^{-1}$ c = O | —O—H |
|---|---|---|---|---|---|
| α-furanose | 0.55 | 62–64° C. | ethyl ether |  |  |
| β-furanose | 0.50 | 86–87° C. | dichloromethane/ ethyl ether | 1730 | 3400 |
| β-pyranose | 0.37 | 116–119° C. | dichloromethane/ ethyl ether | 1720 | 3400 |
| α-pyranose | 0.34 |  |  | 1760 | 3400 |

*TLC performed with the same solvent system as in Example No. 5

| $^{13}$C NMR in CDCl$_3$ | | | | | | | | | |
|---|---|---|---|---|---|---|---|---|---|
|  | $C_1$ | $C_2$ | $C_3$ | $C_4$ | $C_5$ | $C_6$ | —O—$\underline{C}H_2$ | —$CH_3$ | $CH_2$—$\underline{C}H_2$— | —$(CH_2)_{12}$—$CH_3$ |
| β-furanoside | 106.63 | 78.73 | 78.24 | 87.45 | 70.33 | 172.04 | 67.89 | 14.13 | 66.70 | 22.74; 25.82; 26.20; 28.64; 29.29; 29.43; 29.72; 31.97; |
| β-pyranoside | 102.94 | 71.57 | 73.25 | 70.57 | 74.09 | 168.06 | 69.87 | 14.15 | 69.97 | 22.76; 25.91; 26.04; 28.61; 29.35; 29.45; 29.78; 32.03 |
| α-pyranoside | 98.90 | 68.84 |  | 70.49 |  | 169.06 | 69.14 | 14.10 | 67.78 | 22.71; 25.85; 26.12; 28.59; 29.35; 29.40; 29.72; 31.95; |

| $^{13}$C NMR in CDCl$_3$ | | | | | | | | | |
|---|---|---|---|---|---|---|---|---|---|
|  | $C_1$ | $C_2$ | $C_3$ | $C_4$ | $C_5$ | $C_6$ | —O—$\underline{C}H_2$ | $CH_3$ | —$CO_2\underline{C}H_2$— | —$(CH_2)_{14}$—$CH_3$ |
| α-furanose | 100.94 | 78.26 | 75.50 | 82.84 | 70.08 | 172.31 | 69.43 | 14.18 | 66.05 | 22.76; 25.85; 26.12; 28.67; 29.45; 29.78; 32.03; |
| β-furanose | 108.68 |  | 78.59 |  | 87.56 | 70.33 | 172.09 | 67.89 | 14.18 | 66.83 | 22.76; 25.82; |

| | ¹³C NMR in CDCl₃ | | | | | | | | | |
|---|---|---|---|---|---|---|---|---|---|---|
| | $C_1$ | $C_2$ | $C_3$ | $C_4$ | $C_5$ | $C_6$ | —O—$\underline{C}H_2$ | $CH_3$ | —$CO_2\underline{C}H_2$— | —$(\underline{C}H_2)_{14}$—$CH_3$ |
| β-pyranose | 102.99 | 71.36 | 73.25 | 70.63 | 74.12 | 168.17 | 69.92 | 14.20 | 65.97 | 26.23; 29.45; 29.78; 32.03 22.79; 25.93; 28.64; 29.48; 29.81; 32.05; |
| α-pyranose | 99.01 | 68.60 | | 70.44 | | 169.14 | 69.11 | 14.07 | 65.70 | 22.68; 25.85; 26.12; 28.59; 29.37; 29.75; 31.95; |

1) EXAMPLE NO. 9

Preparation of n-octadecyl n-octadecyl D-galactoside uronate (I/R1=R2=n-octadecyl)
Method A 508.5 g (1.88 mole) of n-octadecanol, 800 ml of diglyme and 10.2 g (5.53 ml; 0.10 mole) of concentrated sulphuric acid are added to 200 g (0.94 mole) of D-galacturonic acid monohydrate. The mixture is heated at 60° C. under a vacuum of 18 mm of Hg, for 10 hours. Sodium hydrogen carbonate is then added to the reaction medium until a pH of 7 is obtained. The mixture is allowed to cool; the reaction mixture which solidifies is supplemented with 500 ml of tetrahydrofuran, stirred and filtered on sintered glass No. 3. n-Octadecyl n-octadecyl D-galactoside uronate precipitates from the concentrated filtrate with an overall yield of 94%. Chromatography, similar to that performed in Example 9, makes it possible to isolate the three predominant isomers which precipitate during evaporation of the elution solvents and which are then recrystallized.

| | *Rf | Melting point | Recrystallization solvent | Infrared U:cm⁻¹ | |
|---|---|---|---|---|---|
| | | | | c = O | —O—H |
| β-furanoside | 0.51 | 90–91° C. | dichloromethane/ isopropyl ether | 1730 | 3400 |
| β-pyranoside | 0.39 | 127–129° C. | dichloromethane/ isopropyl ether | 1720 | 3400 |
| α-pyranoside | 0.35 | 98–99° C. | dichloromethane/ isopropyl ether | 1760 | 3400 |

*TLC performed with the same eluent system as in Example No. 5

| | ¹³C NMR in CDCl₃ | | | | | | | | | |
|---|---|---|---|---|---|---|---|---|---|---|
| | $C_1$ | $C_2$ | $C_3$ | $C_4$ | $C_5$ | $C_6$ | —O—$\underline{C}H_2$— | —$CH_3$ | —$CO_2\underline{C}H_2$— | —$(\underline{C}H_2)_{16}$—$CH_3$ |
| β-furanoside | 108.79 | 78.51 | 87.61 | 70.33 | | 172.06 | 67.89 | 14.21 | 66.69 | 22.79; 25.85; 26.27; 28.69; 29.48; 29.81; 32.05; |
| α-pyranoside | 98.63 | 69.24 | | 70.17 | 70.95 | 168.76 | 65.94 | 14.21 | 65.94 | 22.79; 25.91; 26.20; 28.64; 29.45; 29.78; 32.03; |

6) EXAMPLE NO. 10

Preparation of sodium ethyl D-galactoside uronate (I/R1= ethyl and R2=sodium)

A solution of 16 g (0.40 mole) of sodium hydroxide dissolved in 40 ml of water is added to a solution of 100 grams (0.40 mole) of a mixture of ethyl ethyl D-galactoside uronate isomers prepared according to Example 1 in 400 ml of dichloromethane. The mixture is stirred at 25° C. for 3 hours. The residue obtained by evaporation of the solvent is taken up in 300 ml of acetone; the mixture of sodium ethyl D-galactoside uronates which precipitates is filtered, washed with acetone and dried. The yield is quantitative.

Starting with each of the 4 ethyl ethyl D-galactoside uronate isomers purified according to Example 1, each of the 4 pure sodium ethyl D-galactoside uronate isomers, whose physicochemical characteristics are summarized below, is quantitatively obtained according to this same operating procedure.

| $^{13}$C NMR in D$_2$O: the table below gives the chemical shifts in ppm. | | | | | | | | |
|---|---|---|---|---|---|---|---|---|
| | C-1 | C-2 | C-3 | C-4 | C-5 | C-6 | —O—$\underline{C}$H$_2$— | —$\underline{C}$H$_3$ |
| β-furanose | 110.02 | 83.66 | 79.29 | 86.99 | 73.44 | 180.91 | 66.90 | 17.09 |
| α-furanose | 103.19 | 78.78 | 76.73 | 85.44 | 74.40 | | 67.08 | 17.09 |
| β-pyranose | 104.69 | 73.36 | 75.94 | 75.22 | 78.30 | 177.89 | 66.87 | 17.05 |
| α-pyranose | 100.84 | 70.65 | 72.46 | 73.57 | 74.30 | | 66.9 | 17.09 |

11) EXAMPLE NO. 11

Preparation of sodium hexyl D-galactoside uronate (I/R1=hexyl and R2=sodium)

A solution of 11.6 g (0.29 mole) of sodium hydroxide in 30 ml of water is added to a solution of 100 g (0.29 mole) of the mixture of hexyl hexyl D-galactoside uronates obtained according to Example No. 3, in 400 ml of heptane. After reacting for 3 hours at 30° C., evaporating the solvent under reduced pressure and precipitating the residue in 200 ml of acetone and filtering, the mixture of sodium hexyl galactoside uronates is obtained quantitatively.

Starting with the hexyl hexyl α-D-galactopyranoside uronate or hexyl hexyl α-D-galactofuranoside uronate purified according to Example No. 3, sodium hexyl α-D-galactopyranoside uronate or sodium hexyl α-D-galactofuranoside uronate, whose physicochemical characteristics are summarized below, is obtained according to this same operating procedure, still quantitatively:

Method A

A solution of 9.4 g (0.24 mole) of sodium hydroxide in 50 ml of water is added to a solution of 100 g (0.24 mole) of the mixture of octyl octyl D-galactoside uronate prepared according to Example 4 in 200 ml of tetrahydrofuran. After stirring for 1 hour at 30° C., the mixture of sodium octyl D-galactoside uronate which separates is taken up in 200 ml of absolute ethanol. The mixture is stirred for 30 minutes. Crystals which form are filtered, washed with 200 ml of absolute ethanol and then dried. They correspond to the mixture of sodium octyl D-galactoside uronates thus quantitatively obtained.

Starting with each of the 4 octyl octyl D-galactoside uronates purified according to Example 4, each of the 4 pure sodium octyl D-galactoside uronate isomers, whose physicochemical characteristics are summarized below, is quantitatively obtained according to this same procedure.

| $^{13}$C NMR in D$_2$O: the table below gives the chemical shifts in ppm. | | | | | | | | | |
|---|---|---|---|---|---|---|---|---|---|
| | C-1 | C-2 | C-3 | C-4 | C-5 | C-6 | —O—$\underline{C}$H$_2$— | —($\underline{C}$H$_2$)$_n$— | —CH$_2$—$\underline{C}$H$_3$ |
| α-pyranose | 100.86 | 70.97 | 72.17 | 73.36 | 74.17 | 177.88 | 71.02 | 33.62<br>31.35<br>27.76<br>24.66 | 16.08 |
| α-furanose | 109.71 | 83.55 | 79.02 | 86.51 | 71.18 | 180.44 | 73.33 | 33.60<br>31.37<br>27.60<br>24.71 | 16.14 |

12) EXAMPLE NO. 12

Preparation of sodium octyl D-galactoside uronate (I/RI= octyl and R2=sodium)

| $^{13}$C NMR in D$_2$O: the table below gives the chemical shifts in ppm. | | | | | | | | | |
|---|---|---|---|---|---|---|---|---|---|
| | C-1 | C-2 | C-3 | C-4 | C-5 | C-6 | —O—$\underline{C}$H$_2$ | —($\underline{C}$H$_2$)$_n$— | —CH$_2$—$\underline{C}$H$_3$ |
| α-pyranose | 101.27 | 70.77 | 72.40 | 73.71 | 74.56 | 177.97 | 71.38 | 34.52<br>31.95<br>28.64<br>25.23 | 16.55 |
| β-pyranose | 105.33 | 73.12 | 73.39 | 75.73 | 78.41 | 177.56 | 73.12 | 14.37<br>31.80<br>28.23<br>25.16 | 16.48 |
| β-furanose | 110.44 | 83.44 | 78.83 | 86.34 | 71.11 | 180.83 | 73.22 | 34.33<br>31.75<br>28.39<br>25.07 | 16.22 |
| α-furanose | 103.80 | 79.68 | 77.13 | 85.56 | 71.59 | 180.81 | 74.76 | 34.46<br>31.90 | 16.44 |

-continued

| | | | | $^{13}$C NMR in $D_2O$: the table below gives the chemical shifts in ppm. | | | | | |
|---|---|---|---|---|---|---|---|---|---|
| C-1 | C-2 | C-3 | C-4 | C-5 | C-6 | —O—$\underline{C}H_2$ | —($\underline{C}H_2$)$_n$— | —CH$_2$—$\underline{C}H_3$ | |
| | | | | | | | 28.46 | | |
| | | | | | | | 25.20 | | |

Method B 3.84 g (0.096 mole) of sodium hydroxide in solution in 20 ml of water and 0.2 ml of tetrapropylammonium hydroxide are added to 40 g (0.096 mole) of a mixture of octyl octyl D-galactoside uronates in solution in 200 ml of ethylene glycol dimethyl ether. After stirring for 30 minutes at 20° C., the solvent is evaporated under reduced pressure and the residue is taken up in 200 ml of ethyl acetate. The precipitate formed is filtered, washed with ethyl acetate (50 ml) and then dried. The corresponding mixture of sodium octyl D-galactoside uronate is quantitatively obtained.

13) EXAMPLE NO. 13

Preparation of sodium dodecyl β-D-galactofuranoside uronate (I/R1: dodecyl and R2=sodium)

A solution of 7.6 g (0.19 mole) of sodium hydroxide in 20 ml of water is added to a solution of 100 g (0.19 mole) of dodecyl dodecyl β-D-galactofuranoside uronate in 500 ml of absolute ethanol. After stirring for 1 h 30 minutes at 30° C., filtering, washing the precipitate with absolute ethanol (50 ml×4) at 40° C. and drying sodium dodecyl β-D-galactofuranoside uronate, whose physicochemical characteristics are given below, is obtained with a yield which is also greater than 95%:

| | $^{13}$C MR in $D_2O$: the chemical shifts are expressed in ppm. | | | | | | | | |
|---|---|---|---|---|---|---|---|---|---|
| | C-1 | C-2 | C-3 | C-4 | C-5 | C-6 | —O—CH$_2$ | —(CH$_2$)$_n$— | —CH$_2$—$\underline{C}H_3$— |
| β-furanose | 110.50 | 83.82 | 79.76 | 87.26 | 71.05 | 180.59 | 74.33 | 34.83 | 16.45 |
| | | | | | | | | 32.85 | |
| | | | | | | | | 28.86 | |
| | | | | | | | | 25.40 | |

14) EXAMPLE NO. 14

Preparation of ethyl β-D-galactofuranoside uronic acid 50 g (0.2 mole) of sodium ethyl β-D-galactofuranoside uronate prepared according to Example No. 10 are solubilized in water (10% solution).

After passing through a column containing 30 ml of IR 120 H$^+$ resin and concentrating under vacuum, ethyl β-D-galactofuranoside uronic acid, whose physicochemical characteristics are given below, is recovered:

| | $^{13}$C MR in $D_2O$: $^{13}$C CHEMICAL SHIFTS (ppm) IN $D_2O$ | | | | | | | |
|---|---|---|---|---|---|---|---|---|
| | C-1 | C-2 | C-3 | C-4 | C-5 | C-6 | —O—$\underline{C}H_2$ | —$\underline{C}H_3$ |
| β-furanose | 109.90 | 83.57 | 78.70 | 86.07 | 72.93 | 177.91 | 66.90 | 17.09 |

15) EXAMPLE NO. 15

Preparation of ethyl β-D-galactopyranoside uronic acid 100 g (0.4 mol) of sodium ethyl β-D-galactopyranoside uronate prepared according to Example No. 10 is solubilized in water (20% solution). After adding sulphuric acid up to pH=2, concentrating under vacuum and selectively precipitating the salts in acetone, ethyl β-D-galactopyranoside uronic acid is recovered with a 90% yield (80 grams). Its physicochemical characteristics are given below:

| | $^{13}$C NMR in $D_2O$: | | | | | | | |
|---|---|---|---|---|---|---|---|---|
| | C1 | C2 | C3 | C4 | C5 | C6 | OCH$_2$ | —CH$_3$ |
| β-py-ranose | 104.61 | 72.76 | 74.95 | 72.23 | 76.61 | 174.66 | 67.01 | 16.95 |

16) Example No. 16

Preparation of hexyl α-D-galactopyranoside uronic acid 100 g (0.33 mole) of sodium hexyl α-D-galactopyranoside uronate prepared according to Example 11 are solubilized in water (15% solution). After acidification to pH=2, concentrating under vacuum and selectively precipitating the salts in acetone, hexyl α-D-galactopyranoside uronic acid, whose physicochemical characteristics are indicated below, is recovered with a 95% yield:

| | $^{13}$C CHEMICAL SHIFTS (ppm) IN D$_2$O | | | | | | | |
|---|---|---|---|---|---|---|---|---|
| | C-1 | C-2 | C-3 | C-4 | C-5 | C-6 | —(CH$_2$)— | (CH$_2$)$_n$ | —CH$_2$—CH$_3$ |
| (α pyranose) | 101.20 | 70.35 | 71.79 | 72.97 | 73.36 | 175.74 | 71.23 | 34.01<br>31.69<br>28.08<br>24.93 | 16.25 |

17) EXAMPLE NO. 17

Preparation of octyl α-D-galactopyranoside uronic acid 50 g (0.15 mole) of sodium octyl α-D-galactopyranoside uronate prepared according to Example 12 are solubilized in water (30% solution). After passing through 400 ml of a cationic resin of the IR 120 H$^+$ type and concentrating under vacuum, α-D-galactopyranoside uronic acid, whose physicochemical characteristics are indicated below, is quantitatively recovered in the form of a gum:

| | $^{13}$C CHEMICAL SHIFTS (ppm) IN D$_2$O | | | | | | | |
|---|---|---|---|---|---|---|---|---|
| | C-1 | C-2 | C-3 | C-4 | C-5 | C-6 | —(CH$_2$)— | (CH$_2$)$_n$ | —CH$_2$—CH$_3$ |
| (α pyranose) | 101.24 | 70.23 | 71.57 | 72.72 | 72.95 | 174.63 | 71.24 | 31.80<br>34.32<br>25.00<br>28.47 | 16.22 |

18) EXAMPLE NO. 18

Preparation of n-decyl β-D-galactofuranoside uronic acid 20 ml of 2.5N sodium hydroxide are added to 240 mg (0.51 mmol) of n-decyl n-decyl β-D-galactofuranoside uronate solubilized in 5 ml of THF and the mixture is allowed to stand at room temperature for 3 hours. 30 ml of ethyl ether are added and then after decanting, the aqueous phase is washed with 30 ml of ethyl ether. The aqueous phase is acidified with 50% HCl at 0° C. to pH=2 and then extracted three times with 30 ml of ethyl acetate. The organic phases are pooled, washed with 30 ml of water, dried over magnesium sulphate (2 g) and evaporated. 140 mg of n-decyl β-D-galactofuranoside uronic acid are then obtained (82% yield) in the form of a gum. *Rf=0.67 (dichloromethane/methanol-1/1-v/v) *$^{13}$C NMR in CD$_3$OD

19) EXAMPLE NO. 19

Preparation of n-decyl α-D-galactopyranoside uronic acid

The procedure performed on 360 mg (0.7 mmol) of substrate is similar to that described in Example No. 18, but using in place of ethyl acetate an ethyl acetate/n-butanol mixture (1/1-v/v) during the final extractions.

230 mg (90% yield) of n-decyl α-D-galactopyranoside uronic acid, which is in the form of white crystals and whose physicochemical characteristics are indicated below, are obtained: Rf: 0.22 (dichloromethane/methanol-1/1-v/v) $^{13}$C NMR in CD$_3$OD

| C1 | C2 | C3 | C4 | C5 | C6 | —CH$_2$—O— | —CH$_3$ | —(CH$_2$)$_8$—CH$_3$— |
|---|---|---|---|---|---|---|---|---|
| 101.24 | 70.28 | 71.69 | 72.45 | 173.21 | | 70.58 | 15.21 | 24.37; 27.91;<br>31.11; 31.22;<br>31.39; 33.71; |

20) EXAMPLE NO. 20

Preparation of n-decyl β-D-galactopyranoside uronic acid:

The preparation, using 140 mg (0.29 mmol) of n-decyl n-decyl β-D-galactopyranoside uronate as starting material and according to the operating procedure described in Example No. 19, n-decyl β-D-galactopyranoside uronic acid is formed with a yield of 85% (82 mg); it is in the form of

| C1 | C2 | C3 | C4 | C5 | C6 | —CH$_2$—O— | —CH$_3$ | —(CH$_2$)$_8$—CH$_3$— |
|---|---|---|---|---|---|---|---|---|
| 110.12 | 83.96 | 78.76 | 85.66 | 71.09 | 167.16 | 69.76 | 15.21 | 24.42; 27.97;<br>31.25; 31.38;<br>31.46; 33.77; | a white powder, the summary of the physicochemical characteristics of which are indicated below:

Rf: 0.38 (dichloromethane/methanol-1/1-v/v) $^{13}$C NMR in $CD_3OD$

| C1 | C2 | C3 | C4 | C5 | C6 | —($\underline{C}H_2$)—O— | —$\underline{C}H_3$ | —($\underline{C}H_2$)$_8$—$\underline{C}H_3$— |
|---|---|---|---|---|---|---|---|---|
| 105.33 | 72.72 | 75.26 | 72.12 | 76.07 | 172.75 | 71.90 | 15.18 | 24.45; 27.81; 31.17; 31.36; 31.42; 31.46; 33.77; |

EXAMPLE NO. 21

Foaming power of the sodium alkyl galactoside uronates according to the invention (NFT 73404 standard). Compounds I/R1=octyl, decyl, dodecyl, tetradecyl, hexadecyl. R2 is sodium.

FOAM VOLUME AS A FUNCTION OF THE CONCENTRATION

|   | Concentration (g/l) | C8 (ml) | C10 (ml) | C12 (ml) | C14 (ml) | C16 (ml) |
|---|---|---|---|---|---|---|
| 1 | 0.1 | 0 | 80 | 280 | 270 | 120 |
| 2 | 0.25 | 0 | 290 | 250 | 360 | 200 |
| 3 | 0.5 | 20 | 370 | 500 | 400 | 240 |
| 4 | 1 | 100 | 480 | 520 | 400 | 270 |

COMPARATIVE EXAMPLE NO. 22

Comparison of the foaming power of various known surfactants and sodium dodecyl galactoside uronate-I/R1=dodecyl and R2 is sodium (NFT 73404 standard).

|   | Concentration (g/l) | SDBS | SDS | LES | C12 |
|---|---|---|---|---|---|
| 1 | 0.1 | 380 | 380 | 380 | 280 |
| 2 | 0.25 | 400 | 410 | 420 | 450 |
| 3 | 0.5 | 420 | 430 | 440 | 500 |
| 4 | 1 | 440 | 450 | 450 | 520 |

The concentrations are expressed in g/l. The foam volumes in ml.

COMPARATIVE EXAMPLE NO. 23

Comparison of the foaming power of a 1% solution of sodium alkyl galactoside uronate according to the invention (I/R1=octyl, decyl, dodecyl, tetradecyl, hexadecyl and R2 is sodium) and reference products (NFT 7340 standard-25° C.-initial foam volume).

|   | Number of C | Vol. (ml) |
|---|---|---|
| 1 | C8 | 100 |
| 2 | C10 | 480 |
| 3 | C12 | 520 |
| 4 | C14 | 400 |
| 5 | C16 | 270 |

-continued

|   | Number of C | Vol. (ml) |
|---|---|---|
| 6 | 0 | 0 |
| 7 | SDBS | 440 |
| 8 | SDS | 450 |
| 9 | LES | 450 |

EXAMPLE NO. 24

Study of the stability of the foam for the sodium alkyl galactoside uronates according to the invention (I/R1=octyl, decyl, dodecyl, tetradecyl, hexadecyl, and R2 is sodium). NFT 73404 standard.

|   | Time (min) | C8 (ml) | C10 (ml) | C12 (ml) | C14 (ml) | C16 (ml) |
|---|---|---|---|---|---|---|
| 1 | 0 | 100 | 480 | 520 | 400 | 270 |
| 2 | 1 | 90 | 460 | 510 | 390 |   |
| 3 | 2 | 70 | 450 | 510 | 380 | 260 |
| 4 | 5 | 50 | 440 | 500 | 370 | 250 |
| 5 | 10 | 50 | 430 | 490 | 360 | 240 |
| 6 | 15 | 40 | 400 | 480 | 350 | 230 |
| 7 | 20 | 30 | 380 | 460 | 340 | 220 |

COMPARATIVE EXAMPLE NO. 25

Comparative study of the stability of the foam for the sodium alkyl galactoside uronates according to the invention (I/R1=decyl, dodecyl, tetradecyl, and R2 is sodium) and known surfactants. NFT 73404 standard.

|   | Time (min) | SDBS (ml) | SDS (ml) | LES (ml) | C10 (ml) | C12 (ml) |
|---|---|---|---|---|---|---|
| 1 | 0 | 440 | 450 | 450 | 480 | 520 |
| 2 | 1 | 430 | 430 | 430 | 460 | 510 |
| 3 | 2 | 420 | 420 | 420 | 450 | 510 |
| 4 | 5 | 410 | 400 | 400 | 440 | 500 |
| 5 | 10 | 400 | 390 | 390 | 430 | 490 |
| 6 | 15 | 390 | 380 | 380 | 400 | 480 |
| 7 | 20 | 380 | 360 | 370 | 380 | 460 |

EXAMPLE NO. 26

Measurement of the absorption of 1% solutions of the sodium alkyl galactoside uronates according to the invention. Compounds I/R1=octyl, decyl, dodecyl, tetradecyl, hexadecyl and R2 is sodium. KRUSS tensiometer-25° C.

| Time (min) | C8 1% | C10 1% | C12 1% | C14 1% | C16 1% |
|---|---|---|---|---|---|
| 1 | 0 | 0 | 0 | 0 | 0 | 0 |
| 2 | 10 | 0.15 | 0.2 | 0.09 | 0.025 | 0.01 |
| 3 | 20 | 0.19 | 0.27 | 0.11 | 0.045 | 0.015 |
| 4 | 30 | 0.215 | 0.3 | 0.13 | 0.055 | 0.018 |
| 5 | 40 | 0.24 | 0.32 | 0.14 | 0.06 | 0.02 |
| 6 | 50 | 0.25 | 0.33 | 0.155 | 0.07 | 0.025 |
| 7 | 60 | 0.265 | 0.335 | 0.165 | 0.075 | 0.025 |
| 8 | 80 | 0.29 | 0.34 | 0.18 | 0.08 | 0.03 |
| 9 | 100 | 0.31 | 0.35 | 0.19 | 0.085 | 0.03 |
| 10 | 120 | 0.315 | 0.355 | 0.195 | 0.09 | 0.035 |
| 11 | 140 | 0.325 | 0.36 | 0.2 | 0.092 | 0.035 |
| 12 | 160 | 0.335 | 0.363 | 0.205 | 0.095 | 0.04 |
| 13 | 180 | 0.345 | 0.365 | 0.205 | 0.097 | 0.04 |
| 14 | 200 | 0.35 | 0.37 | 0.21 | 0.1 | 0.045 |
| 15 | 240 | 0.355 | 0.375 | 0.215 | 0.11 | 0.048 |
| 16 | 280 | 0.355 | 0.38 | 0.22 | 0.115 | 0.05 |
| 17 | 320 | 0.355 | 0.385 | 0.222 | 0.125 | 0.052 |
| 18 | 360 | 0.355 | 0.39 | 0.222 | 0.13 | 0.055 |
| 19 | 400 | 0.355 | 0.395 | 0.225 | 0.14 | 0.055 |
| 20 | 440 | 0.36 | 0.4 | 0.23 | 0.145 | 0.055 |
| 21 | 480 | 0.36 | 0.41 | 0.23 | 0.15 | 0.055 |
| 22 | 520 | 0.36 | 0.415 | 0.23 | 0.155 | 0.055 |
| 23 | 560 | 0.36 | 0.42 | 0.235 | 0.165 | 0.055 |
| 24 | 600 | 0.36 | 0.425 | 0.235 | 0.17 | 0.055 |

COMPARATIVE EXAMPLE NO. 27

Comparative measurement of the absorption of 1% solutions of known surfactants and decyl decyl galactoside uronate (compound I) R1=decyl and R2 is sodium. KRUSS tensiometer-25° C.

| | Time (min) | C10 (g) | APG (g) | SDSB (g) | LES (g) | SDS (g) |
|---|---|---|---|---|---|---|
| 1 | 0 | 0 | 0 | 0 | 0 | 0 |
| 2 | 10 | 0.2 | 0.265 | 0.23 | 0.18 | 0.2 |
| 3 | 20 | 0.27 | 0.35 | 0.3 | 0.225 | 0.24 |
| 4 | 30 | 0.3 | 0.38 | 0.34 | 0.25 | 0.26 |
| 5 | 40 | 0.32 | 0.38 | 0.36 | 0.28 | 0.27 |
| 6 | 50 | 0.33 | 0.38 | 0.37 | 0.3 | 0.275 |
| 7 | 60 | 0.335 | 0.385 | 0.375 | 0.305 | 0.28 |
| 8 | 80 | 0.34 | 0.385 | 0.375 | 0.335 | 0.285 |
| 9 | 100 | 0.35 | 0.385 | 0.38 | 0.34 | 0.29 |
| 10 | 120 | 0.355 | 0.385 | 0.38 | 0.355 | 0.295 |
| 11 | 140 | 0.36 | 0.39 | 0.385 | 0.36 | 0.3 |
| 12 | 160 | 0.363 | 0.39 | 0.385 | 0.36 | 0.305 |
| 13 | 180 | 0.365 | 0.39 | 0.385 | 0.36 | 0.31 |
| 14 | 200 | 0.37 | 0.39 | 0.385 | 0.36 | 0.315 |
| 15 | 240 | 0.375 | 0.395 | 0.39 | 0.365 | 0.315 |
| 16 | 280 | 0.38 | 0.395 | 0.39 | 0.365 | 0.32 |
| 17 | 320 | 0.385 | 0.395 | 0.39 | 0.365 | 0.325 |
| 18 | 360 | 0.39 | 0.395 | 0.395 | 0.365 | 0.33 |
| 19 | 400 | 0.395 | 0.395 | 0.395 | 0.365 | 0.335 |
| 20 | 440 | 0.4 | 0.395 | 0.395 | 0.365 | 0.338 |
| 21 | 480 | 0.41 | 0.395 | 0.395 | 0.365 | 0.34 |
| 22 | 520 | 0.415 | 0.395 | 0.395 | 0.365 | 0.345 |
| 23 | 560 | 0.42 | 0.395 | 0.395 | 0.365 | 0.347 |
| 24 | 600 | 0.425 | 0.395 | 0.395 | 0.365 | 0.35 |

EXAMPLE NO. 28

Measurements of the wetting angle, on polyethylene, of 1% solutions of alkyl galactoside uronates according to the invention (compound I). R1=decyl, dodecyl, tetradecyl, hexadecyl, octadecyl and R2 is sodium. KRUSS tensiometer-25° C.

COMPARATIVE EXAMPLE 29

Comparative measurements of the wetting angle of a 1% solution of sodium decyl galactoside uronate (compound I/R1=decyl and R2 is sodium) and known surfactants.

| Surfactants (1%) | Angle of contact (°) |
|---|---|
| GAC10 | 4 |
| GAC12 | 20 |
| GAC14 | 55 |
| GAC16 | 60 |
| GAC18 | 68 |
| SDBS | 22 |
| SDS | 60 |
| LES | 62 |

EXAMPLE NO. 30

Measurement of the surface tensions of 1% solutions of sodium alkyl galactoside uronate according to the invention (compound I/R1=octyl, decyl, dodecyl, tetradecyl, hexadecyl, octadecyl and R2 is sodium).

COMPARATIVE EXAMPLE NO. 31

Comparative measurements of the surface tensions of the 1% solution of sodium octyl galactoside uronate (I/R1=octyl and R2 is sodium) and solutions of known surfactants.

| Surfactants (1%) | γ(mN/m) |
|---|---|
| GAC8 | 23 |
| GAC10 | 23 |
| GAC12 | 30 |
| GAC14 | 33 |
| GAC16 | 40 |
| GAC18 | 44 |
| APG | 26 |
| SDBS | 30 |
| SDS | 35 |
| LES | 35 |

EXAMPLE NO. 32

Critical micelle concentrations of the sodium alkyl galactoside uronates according to the invention (compound I/R1= octyl, decyl, dodecyl, tetradecyl, hexadecyl, octadecyl, and R2 is sodium).

| Number of C | C.M.C. (g/l) |
|---|---|
| 8 | 11 |
| 10 | 6 |
| 12 | 3 |
| 14 | 1.2 |
| 16 | 0.7 |
| 18 | 0.3 |

EXAMPLES NO. 33 TO 35:
FORMULAE FOR POWDERED DETERGENTS

| | 33 | 34 | 35 |
|---|---|---|---|
| Lauryl benzenesulphonate | 2 | 0 | 5 |
| Sodium decyl D-galactoside uronate | 10 | 20 | 10 |

EXAMPLES NO. 33 TO 35:
FORMULAE FOR POWDERED DETERGENTS

|  | 33 | 34 | 35 |
|---|---|---|---|
| α-Olefinsulphonate | 0 | 10 | 0 |
| Sodium dodecyl D-galactoside uronate | 0 | 0 | 10 |
| Octyl octyl D-galactoside uronate | 4 | 4 | 0 |
| Decyl decyl D-galactoside uronate | 0 | 4 | 0 |
| Dodecyl dodecyl D-galactoside uronate | 0 | 0 | 2 |
| Cocoyl poly(ethylene glycol) ether | 2 | 2 | 10 |
| Silicone oil | 2 | 2 | 0.2 |
| Zeolite 4 Å | 25 | 20 | 25 |
| Sodium carbonate | 8 | 15 | 10 |
| Sodium nitrilotriacetate | 3 | 1 | 1 |
| Sodium citrate | 1 | 0 | 0 |
| Clay | 0 | 4 | 3 |
| Sodium perborate | 20 | 4 | 3 |
| Ethylene-diamine tetraacetyl | 1 | 0 | 0 |
| Ethylene-diamine tetraacetate | 0.5 | 0 | 0 |
| Sodium salt of carboxymethylcellulose | 1 | 2 | 0.3 |
| Enzymes | 0.5 | 0.4 | 1 |
| Optical whiteners | 0.2 | 0.5 | 0.1 |
| Sodium silicate | 4 | 10 | 10 |
| Perfume | qs | qs | qs |
| Water | balance | balance | balance |

EXAMPLES NO. 36 TO 38:
FORMULAE FOR LIQUID DETERGENTS

|  | 36 | 37 | 38 |
|---|---|---|---|
| Alkyl benzenesulphonate | 5 | 0 | 5 |
| Soaps | 10 | 0 | 15 |
| Fatty alcohol ether sulphate | 0 | 2 | 5 |
| Sodium dodecyl D-galactoside uronate | 0 | 20 | 5 |
| Sodium decyl D-galactoside uronate | 10 | 0 | 10 |
| Alkyl poly(ethylene glycol) ether | 10 | 0 | 0 |
| Decyl decyl D-galactoside uronate | 5 | 10 | 0 |
| Dimethylammonium chloride | 0 | 0 | 4 |
| Fatty acid alkanolamide | 1 | 0 | 0 |
| Proteases | 0.5 | 0.5 | 0 |
| Sodium citrate | 2 | 4 | 5 |
| Zeolites | 0 | 20 | 0 |
| Sodium silicate | 1 | 0 | 0 |
| Ethanol/propylene glycol | 10 | 8 | 13 |
| Polycarboxylates | 0 | 2 | 5 |
| Optical whiteners | qs | qs | qs |
| Stabilizers (monoethanolamide) | 3 | 0 | 3 |
| Perfumes | qs | qs | qs |
| Colorants | qs | qs | qs |
| Water | 42.5 | 30 | 28 |

EXAMPLES NO. 39 TO 42:
FORMULATIONS FOR WASHING-UP LIQUIDS

|  | 39 | 40 | 41 | 42 |
|---|---|---|---|---|
| Sodium decyl D-galactoside uronate | 0 | 0 | 0 | 10 |
| Sodium dodecyl D-galactoside uronate | 20 | 20 | 10 | 10 |
| Octyl octyl D-galactoside uronate | 0 | 0 | 5 | 0 |
| Ethoxylated fatty acid monoethanolamide | 5 | 5 | 5 | 0 |
| Lauryl diethanolamide | 0 | 0 | 3 | 10 |
| Sodium polyoxy ethylene lauryl sulphate | 0 | 0 | 10 | 0 |
| Sodium chloride | 3 | 3 | 0 | 0 |
| Sodium acrylate | 0.2 | 0 | 0 | 0 |
| EDTA | 0 | 0.3 | 0 | 0 |
| Ethanol | 0 | 0 | 0 | 3 |
| Propylene glycol | 0 | 0 | 0.2 | 0 |
| Amine oxide | 0 | 0 | 1 | 0 |
| Perfumes | qs | qs | qs | qs |
| Colorants | qs | qs | qs | 13 |
| Preservatives | 0.5 | 0.5 | qs | qs |
| Water | qs 100 | qs 100 | qs 100 | qs 100 |

EXAMPLES NO. 43 TO 46:
FORMULATIONS FOR GENTLE LIQUID SOAPS

|  | 43 | 44 | 45 | 46 |
|---|---|---|---|---|
| Octyl octyl D-galactoside uronate | 0 | 5 | 0 | 0 |
| Sodium decyl D-galactoside uronate | 10 | 5 | 0 | 0 |
| Sodium dodecyl D-galactoside uronate | 0 | 0 | 0 | 10 |
| Sodium tetradecyl D-galactoside uronate | 0 | 0 | 15 | 0 |
| Dodecyl dodecyl D-galactoside uronate | 0 | 2 | 0 | 0 |
| Tetradecyl tetradecyl D-galactoside uronate | 0 | 0 | 0 | 3 |
| Sodium lauryl sulphate | 0 | 5 | 0 | 0 |
| Sodium cocoyl isothionate | 5 | 0 | 0 | 0 |
| Sodium salt of alkyl peptide | 0 | 0 | 0 | 3 |
| Cocoamidopropylbetaine | 5 | 0 | 5 | 0 |
| Wheat protein hydrolysate | 0 | 0 | 2 | 0 |
| Propylene glycol | 0 | 0 | 0 | 4 |
| Sodium chloride | 3 | 2 | 2 | 0 |
| EDTA | 0.3 | 0.3 | 0.3 | 0.3 |
| Cetyl alcohol | 0 | 0 | 0 | 3 |
| Heavy mineral oil | 0 | 0 | 0 | 15 |
| Cocoamidodiethanolamide | 5 | 0 | 5 | 0 |
| Hydroxymethylcellulose | 0 | 0 | 0 | 0.5 |
| Preservatives | qs | qs | qs | qs |
| Disinfectants | 0 | 0 | 0 | 0.2 |
| Perfumes | qs | qs | qs | qs |
| Water | qs 100 | qs 100 | qs 100 | qs 100 |

EXAMPLES NO. 47 TO 50:
FORMULATIONS FOR SHAMPOOS

|  | 47 | 48 | 49 | 50 |
|---|---|---|---|---|
| Sodium dodecyl D-galactoside uronate | 0 | 0 | 10 | 0 |
| Sodium tetradexyl D-galactoside uronate | 10 | 10 | 5 | 5 |
| Disodium lauryl ether sulphosuccinate | 0 | 5 | 0 | 0 |
| 30% cocoamidopropylbetaine | 5 | 10 | 10 | 5 |
| Copra fatty acid diethanolamide | 0 | 0 | 0 | 5 |
| Wheat protein hydrolysate | 0 | 0 | 0 | 2 |
| Octadecyl polyethylene glycol | 10 | 0 | 0 | 0 |
| Triethylene glycol | 1 | 2 | 0 | 0 |
| Sodium chloride | 0 | 1.5 | 1.5 | 2 |
| Preservatives | 0.5 | 0.4 | 0.4 | 0.4 |
| EDTA | 0.3 | 0.3 | 0.3 | 0.3 |
| Perfumes | qs | qs | qs | qs |
| Water | qs 100 | qs 100 | qs 100 | qs 100 |

EXAMPLES NO. 51 TO 52:
FORMULATIONS FOR BATH FOAMS

|  | 51 | 52 |
|---|---|---|
| Sodium dodecyl D-galactoside uronate | 20 | 25 |
| Sodium hexadecyl D-galactoside uronate | 1.2 | 0 |
| Cocoyl monoethanolamide | 5 | 5 |
| Lauryl amidopropylbetaine | 2 | 0 |
| Lauryl amidodimethylbetaine | 0 | 2 |
| Triethylene glycol | 2 | 0 |
| Sweet almond oil | 6 | 5 |
| Ethoxylated sorbitan laurate | 2 | 2 |

EXAMPLES NO. 51 TO 52: FORMULATIONS FOR BATH FOAMS

| | 51 | 52 |
|---|---|---|
| Ethoxylated propylene glycol dioleate | 0 | 2 |
| Lauryl myristyl containing 30 E | 2 | 0 |
| EDTA | 0.3 | 0.3 |
| Sodium chloride | 2 | qs |
| Oleyl acrylate | 0 | 2 |
| Preservative | 0.5 | qs |
| Hexadecanol | 1 | 1 |
| Perfumes | qs | qs |
| Water | qs 100 | qs 100 |

EXAMPLES NO. 53 TO 54: FORMULATIONS FOR A SHOWER GEL

| | 53 | 54 |
|---|---|---|
| Sodium decyl D-galactoside uronate | 25 | 0 |
| Sodium tetradecyl D-galactoside uronate | 0 | 15 |
| Sodium hexadecyl D-galactoside uronate | 0 | 1 |
| Ethoxylated propylene glycol dioleate | 2 | 0 |
| Lauryl amidopropylbetaine | 2 | 0 |
| Acrylic gel | 0 | 0.2 |
| EDTA | 0.3 | 0.3 |
| Sodium chloride | 2 | 0 |
| Pearling agents | 0 | 5 |
| Perfume | 0.2 | 0 |
| Preservatives | 0.5 | 0.5 |
| Water | qs 100 | qs 100 |

We claim:

1. A galacturonic acid derivative having the formula

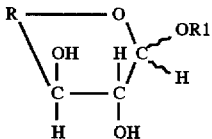
(I)

wherein

R1 represents linear or branched alkyl having 8–22 carbon atoms, and

R represents

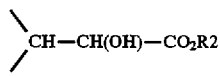

or

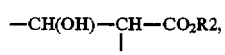

wherein

R2 is the same as R1 and wherein the carbon atom carrying the hydroxyl group is not attached to the endocyclic oxygen atom.

2. The derivative of claim 1 wherein R1 is alkyl having 14 to 22 carbon atoms.

3. The derivative of claim 1 wherein R1 is alkyl having 8 to 14 carbon atoms.

4. The derivative of claim 3 wherein R1 is decyl.

5. A process for imparting surfactant properties to a composition comprising incorporating into said composition from 0.1 to 60 percent by weight a derivative of the formula

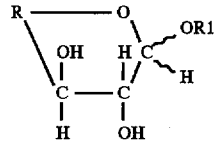
(I)

wherein

R1 represents linear or branched alkyl having 8–22 carbon atoms and

R represents

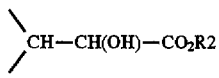

or

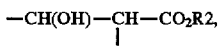

wherein

R2 is the same as R1 and wherein the carbon atom carrying the hydroxyl group is not attached to the endocyclic oxygen atom.

6. A detergent composition comprising 0.1 to 60 percent by weight of a detergent and 99.9 percent to 40 percent by weight of adjuvants, said detergent comprising a galacturonic acid derivative having the formula

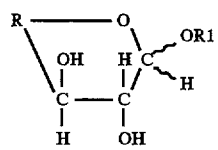
(I)

wherein

R1 represents linear or branched alkyl having 8–22 carbon atoms, and

R represents

or

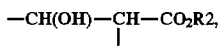

wherein

R2 is the same as R1 and wherein the carbon atom carrying the hydroxyl group is not attached to the endocyclic oxygen group.

7. The detergent composition of claim 6 wherein R1 is alkyl having 8 to 14 carbon atoms.

8. A cosmetic composition comprising 0.1 to 50 percent by weight of an active substance and 99.9 to 50 percent by weight of an excipient, said active substance comprising a galacturonic acid derivative having the formula

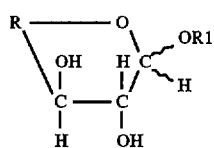 (I)
R1 represents linear or branched alkyl having 8–22 carbon atoms, and
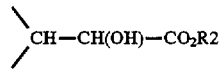
or
—CH(OH)—CH—CO₂R2,
wherein
R2 is the same as R1 and wherein the carbon atom carrying the hydroxyl group is not attached to the endocyclic oxygen group.
* * * * *